(12) United States Patent
Peine et al.

(10) Patent No.: US 12,245,900 B2
(45) Date of Patent: Mar. 11, 2025

(54) SYSTEM AND APPARATUS FOR EXTERNAL TORQUE OBSERVATION AND COMPENSATION FOR SURGICAL ROBOTIC ARM

(71) Applicant: Covidien LP, Mansfield, MA (US)

(72) Inventors: William J. Peine, Ashland, MA (US); Andreas Tobergte, Munich (DE)

(73) Assignee: Covidien LP, Mansfield, MA (US)

( * ) Notice: Subject to any disclaimer, the term of this patent is extended or adjusted under 35 U.S.C. 154(b) by 528 days.

(21) Appl. No.: 17/616,425

(22) PCT Filed: Jul. 9, 2019

(86) PCT No.: PCT/US2019/040908
§ 371 (c)(1),
(2) Date: Dec. 3, 2021

(87) PCT Pub. No.: WO2020/246997
PCT Pub. Date: Dec. 10, 2020

(65) Prior Publication Data
US 2022/0233271 A1  Jul. 28, 2022

Related U.S. Application Data

(60) Provisional application No. 62/856,257, filed on Jun. 3, 2019.

(51) Int. Cl.
*A61B 90/00* (2016.01)
*A61B 34/30* (2016.01)
(Continued)

(52) U.S. Cl.
CPC ............. *A61B 90/06* (2016.02); *A61B 34/30* (2016.02); *B25J 9/1633* (2013.01); *G16H 40/63* (2018.01);
(Continued)

(58) Field of Classification Search
CPC ... A61B 90/06; A61B 34/30; A61B 2090/066; G16H 40/63; B25J 9/1633; G05B 2219/37624; G05B 2219/45117
See application file for complete search history.

(56) References Cited

U.S. PATENT DOCUMENTS 4,926,105 A * 5/1990 Mischenko ............ H02P 21/06
318/800
2013/0211782 A1 8/2013 Rosenberg et al.
(Continued)

FOREIGN PATENT DOCUMENTS

CN 109288592 A 2/2019
EP 3135444 A1 3/2017
(Continued)

OTHER PUBLICATIONS

International Search Report and Written Opinion dated Mar. 3, 2020 issued in corresponding PCT Appln. No. PCT/US2019/040908.
(Continued)

*Primary Examiner* — Basil T. Jos
*Assistant Examiner* — Jay Khandpur
(74) *Attorney, Agent, or Firm* — Carter, DeLuca & Farrell LLP (57) ABSTRACT

A surgical robotic arm includes a first link; a second link coupled to the first link at a first joint such that at least one of the first link or the second link is movable relative to each other; and a first actuator configured to move at least one of the first link or the second link. The surgical robotic arm also includes a joint torque sensor disposed within the first joint and configured to measure torque imparted on at least one of the first link or the second link to obtain a measured torque value. The surgical robotic arm further includes a controller configured to: determine an estimated joint torque value; compare the estimated joint torque value to the measured torque value; and determine an environmental torque value (Continued)

based on a comparison of the estimated joint torque value and the measured torque value.

6 Claims, 8 Drawing Sheets

(51) Int. Cl.
*B25J 9/16* (2006.01)
*G16H 40/63* (2018.01)

(52) U.S. Cl.
CPC .................. *A61B 2090/066* (2016.02); *G05B 2219/37624* (2013.01); *G05B 2219/45117* (2013.01)

(56) References Cited

U.S. PATENT DOCUMENTS

| | | |
|---|---|---|
| 2016/0089211 A1 | 3/2016 | Bowling |
| 2016/0193731 A1 | 7/2016 | Sattler et al. |
| 2016/0361125 A1 | 12/2016 | Balicki et al. |
| 2017/0007336 A1 | 1/2017 | Tsuboi |
| 2017/0128136 A1 | 5/2017 | Post |
| 2017/0197312 A1* | 7/2017 | Osada .................. B25J 9/1676 |
| 2018/0079090 A1* | 3/2018 | Koenig .................. G01L 3/14 |
| 2018/0080841 A1* | 3/2018 | Cordoba ................ A61B 34/35 |
| 2018/0289445 A1 | 10/2018 | Krinninger et al. |
| 2019/0105785 A1 | 4/2019 | Meyer et al. |
| 2020/0001471 A1* | 1/2020 | Chen .................... B25J 13/081 |
| 2020/0369333 A1* | 11/2020 | Lavalley ............... B25J 11/0035 |

FOREIGN PATENT DOCUMENTS

| | | |
|---|---|---|
| WO | 2019063146 A1 | 4/2019 |
| WO | 2019074669 A1 | 4/2019 |

OTHER PUBLICATIONS

Extended European Search Report issued in corresponding application EP 19931819.7 dated May 24, 2023 (13 pages).

Office Action issued in corresponding Chinese application No. 201980001213.7 dated Dec. 8, 2023, together with English language translation (14 pages).

* cited by examiner

SYSTEM AND APPARATUS FOR EXTERNAL TORQUE OBSERVATION AND COMPENSATION FOR SURGICAL ROBOTIC ARM

CROSS-REFERENCE TO RELATED APPLICATION

This application is a National Stage Application under 35 U.S.C. § 371 (a) of PCT/US2019/040908, filed Jul. 9, 2019, which claims the benefit of and priority to U.S. Provisional Patent Application No. 62/856,257 filed Jun. 3, 2019. The entire contents of all of the foregoing applications are incorporated by reference herein.

BACKGROUND

Surgical robotic systems are currently being used in minimally invasive medical procedures. Some surgical robotic systems may include a surgical console controlling a surgical robotic arm and a surgical instrument having an end effector (e.g., forceps or grasping tool) coupled to and actuated by the robotic arm.

The robotic arm may be affected by a variety of external forces. As such there is a need for monitoring such forces and for compensating for these forces in order to improve operation of the robotic arm.

SUMMARY

According to one embodiment of the present disclosure, a surgical robotic arm is disclosed. The surgical robotic arm includes: a first link; a second link coupled to the first link at a first joint such that at least one of the first link or the second link is movable relative to each other; and a first actuator configured to move at least one of the first link or the second link. The surgical robotic arm also includes a joint torque sensor disposed within the first joint and configured to measure torque imparted on at least one of the first link or the second link to obtain a measured torque value. The surgical robotic arm further includes a controller configured to: calculate an input motor torque command in response to a movement command, the input motor torque command configured to activate the first actuator to move at least one of the first link or the second link according to the movement command; determine an estimated joint torque value; determine an environmental torque value based on a comparison of the estimated joint torque value and the measured torque value; and detect a collision based on the environmental torque value being above a threshold.

According to one aspect of the above embodiment, the controller is further configured to adjust the input motor torque command in response detection of the collision. The controller is further configured to adjust the input motor torque command to prevent oversaturating output torque of the first actuator.

According to another aspect of the above embodiment, the surgical robotic arm further includes a motor torque sensor configured to measure the output torque imparted by the first actuator. The controller is further configured to determine a frictional loss for the first actuator and a frictional loss for the first joint. The controller is further configured to determine a gravity effect on at least one of the first link or the second link. The controller is further configured to determine a motor inertia of the first actuator and a joint inertia of at least one of the first link or the second link.

According to another embodiment of the present disclosure, a surgical robotic system is disclosed. The surgical robotic system includes a surgical console including at least one user interface device configured to generate a user input; a control tower coupled to the surgical console and configured to process the user input to generate a movement command; and a surgical robotic arm. The surgical robotic arm includes: a first link; a second link coupled to the first link at a first joint such that at least one of the first link or the second link is movable relative to each other; and a first actuator configured to move at least one of the first link or the second link. The surgical robotic arm also includes a joint torque sensor disposed within the first joint and configured to measure torque imparted on at least one of the first link or the second link to obtain a measured torque value. The surgical robotic arm further includes a controller configured to: calculate an input motor torque command in response to a movement command, the input motor torque command configured to activate the first actuator to move at least one of the first link or the second link according to the movement command; determine an estimated joint torque value; determine an environmental torque value based on a comparison of the estimated joint torque value and the measured torque value; and detect a collision based on the environmental torque value being above a threshold.

According to one aspect of the above embodiment, the controller is further configured to determine the estimated joint torque value based on the torque imparted by the first actuator, the frictional loss for the first actuator, the frictional loss for the first joint, the motor inertia of the first actuator, the joint inertia, and the gravity effect. The controller is further configured to adjust the input motor torque command in response detection of the collision. The controller is further configured to adjust the input motor torque command to prevent oversaturating output torque of the first actuator.

According to another aspect of the above embodiment, the surgical robotic arm further incudes: a motor torque sensor configured to measure a torque imparted by the first actuator. The controller is further configured to determine a frictional loss for the first actuator and a frictional loss for the first joint. The controller is further configured to determine a gravity effect on at least one of the first link or the second link. The controller is further configured to determine a motor inertia of the first actuator and a joint inertia of at least one of the first link or the second link. The controller is further configured to determine the estimated joint torque value based on the torque imparted by the first actuator, the frictional loss for the first actuator, the frictional loss for the first joint, the motor inertia of the first actuator, the joint inertia, and the gravity effect.

According to a further embodiment of the present disclosure, the method further includes: generating a user input through at least one user interface of a surgical console; processing the user input to generate a movement command at a control tower coupled to the surgical console; transmitting the movement command to a controller of a surgical robotic arm. The surgical robotic arm includes: a first link; a second link coupled to the first link at a first joint such that at least one of the first link or the second link is movable relative to each other; and a first actuator configured to move at least one of the first link or the second link. The method further includes: measuring torque imparted on at least one of the first link or the second link to obtain a measured torque value at a joint torque sensor disposed within the first joint; calculating an input motor torque command in response to a movement command, the input motor torque command configured to activate the first actuator to move at least one of the first link or the second link according to the movement command; determining an estimated joint torque value; determining an environmental torque value based on a comparison of the estimated joint torque value and the measured torque value; and detecting a collision based on the environmental torque value being above a threshold.

According to one aspect of the above embodiment, the method further includes: measuring a torque imparted by the first actuator at a motor torque sensor coupled to the first actuator; determining a frictional loss for the first actuator and a frictional loss for the first joint; determining a gravity effect on at least one of the first link or the second link; and determining a motor inertia of the first actuator and a joint inertia of at least one of the first link or the second link.

According to another aspect of the above embodiment, the method further includes determining the estimated joint torque value based on the torque imparted by the first actuator, the frictional loss for the first actuator, the frictional loss for the first joint, the motor inertia of the first actuator, the joint inertia, and the gravity effect. The method further includes, adjusting the input motor torque command in response detection of the collision to prevent oversaturating output torque of the first actuator.

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

As will be described in detail below, the present disclosure is directed to a surgical robotic system, which includes a surgical console, a control tower, and one or more mobile carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command. The controller is further configured to measure total joint torque and to determine estimated joint torque, which includes internal and external forces. The estimated torque is calculated using torque generated by the actuator, which is measured by the actuator's torque sensor, gear and joint friction as calculated using a friction model, effects of gravity on the robotic arm and/or the setup arm as calculated using a gravity model, and actuator and joint inertia calculated using mass and actuator speed. The controller is further configured to compare the measured total joint torque to the estimated torque to determine if environmental torque, e.g., that due to collision, is responsible for the difference between the measured torque and estimated torque. Thus, in situations where there is no collision or other external forces aside from gravity acting on the robotic arm, the environmental torque is about zero, as such the estimated torque and the measured torque, which includes gravity, friction, inertia, and the environmental torque, are about the same. The threshold may be adjusted to vary the sensitivity of the calculations and identification of environmental torque.

Figure 1:
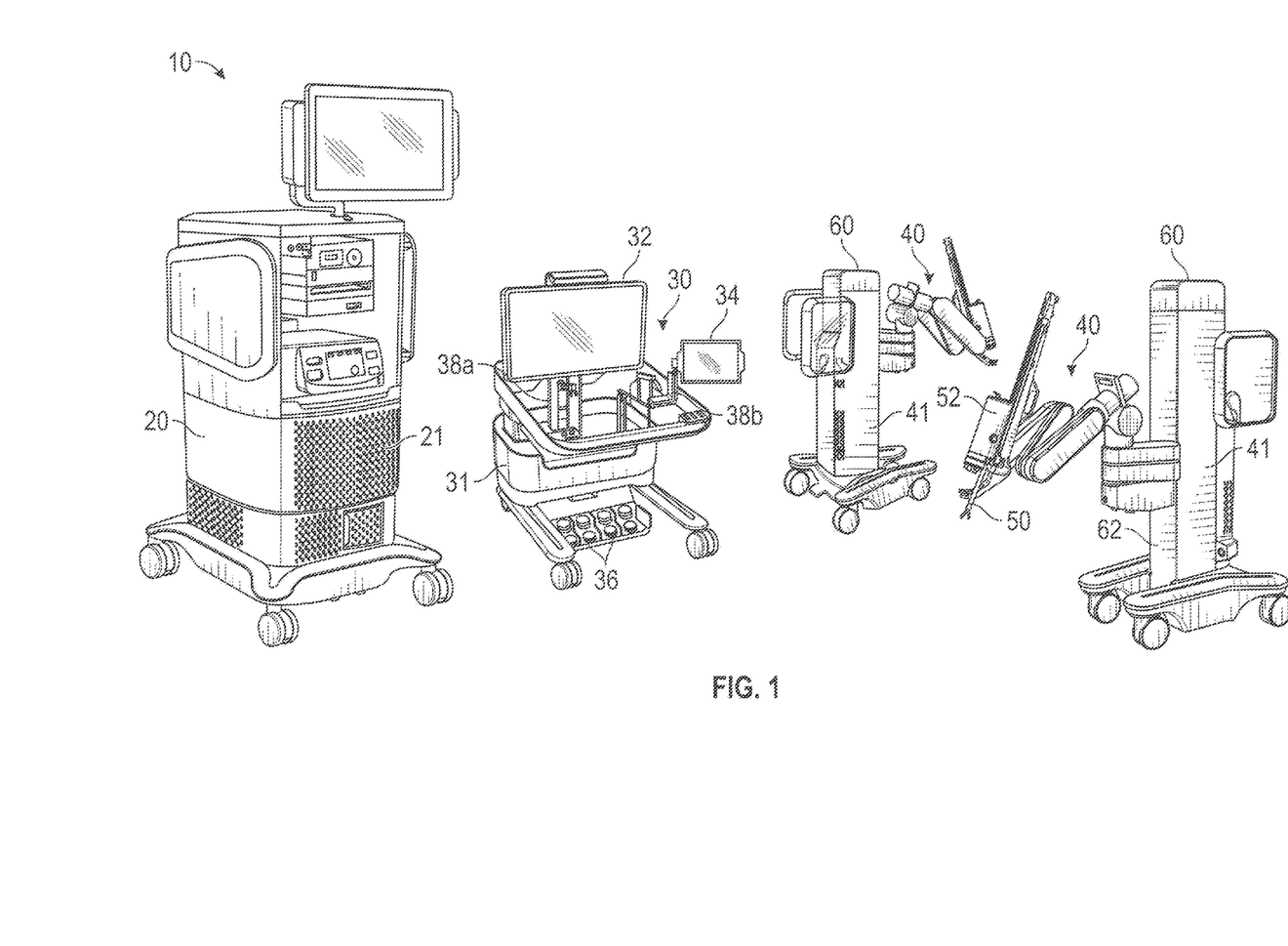
FIG. 1 is a schematic illustration of a surgical robotic system including a control tower, a console, and one or more surgical robotic arms according to the present disclosure.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. The surgical instrument 50 is configured for use during minimally invasive surgical procedures. In embodiments, the surgical instrument 50 may be configured for open surgical procedures. Each of the robotic arms 40 is also coupled to a movable cart 60.

The surgical console 30 includes a first display device 32, which displays a surgical site provided by cameras (not shown) disposed on the robotic arms 40, and a second display device 34, which displays a user interface for controlling the surgical robotic system 10. The surgical console 30 also includes a plurality of user interface devices, such as foot pedals 36 and a pair of handle controllers 38a and 38b which are used by a clinician to remotely control robotic arms 40.

The control tower 20 acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
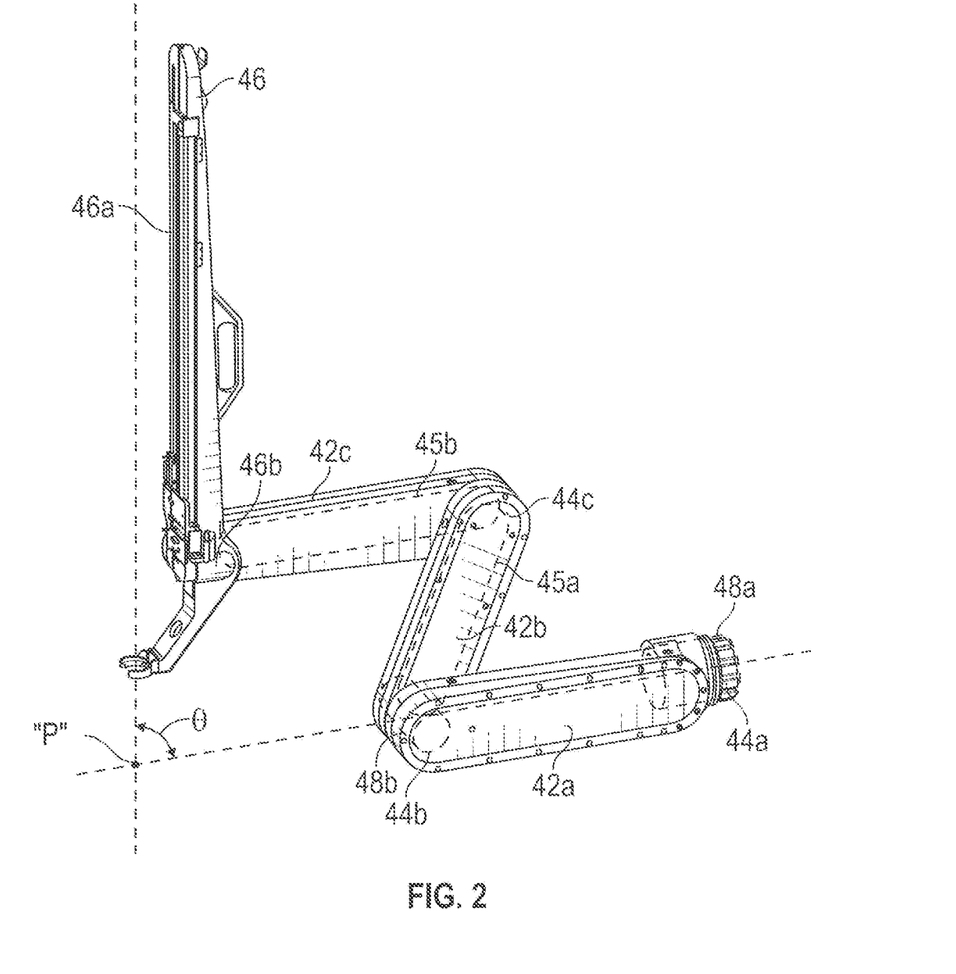
FIG. 2 is a perspective view of a surgical robotic arm of the surgical robotic system of FIG. 1 according to the present disclosure.
Figure 3:
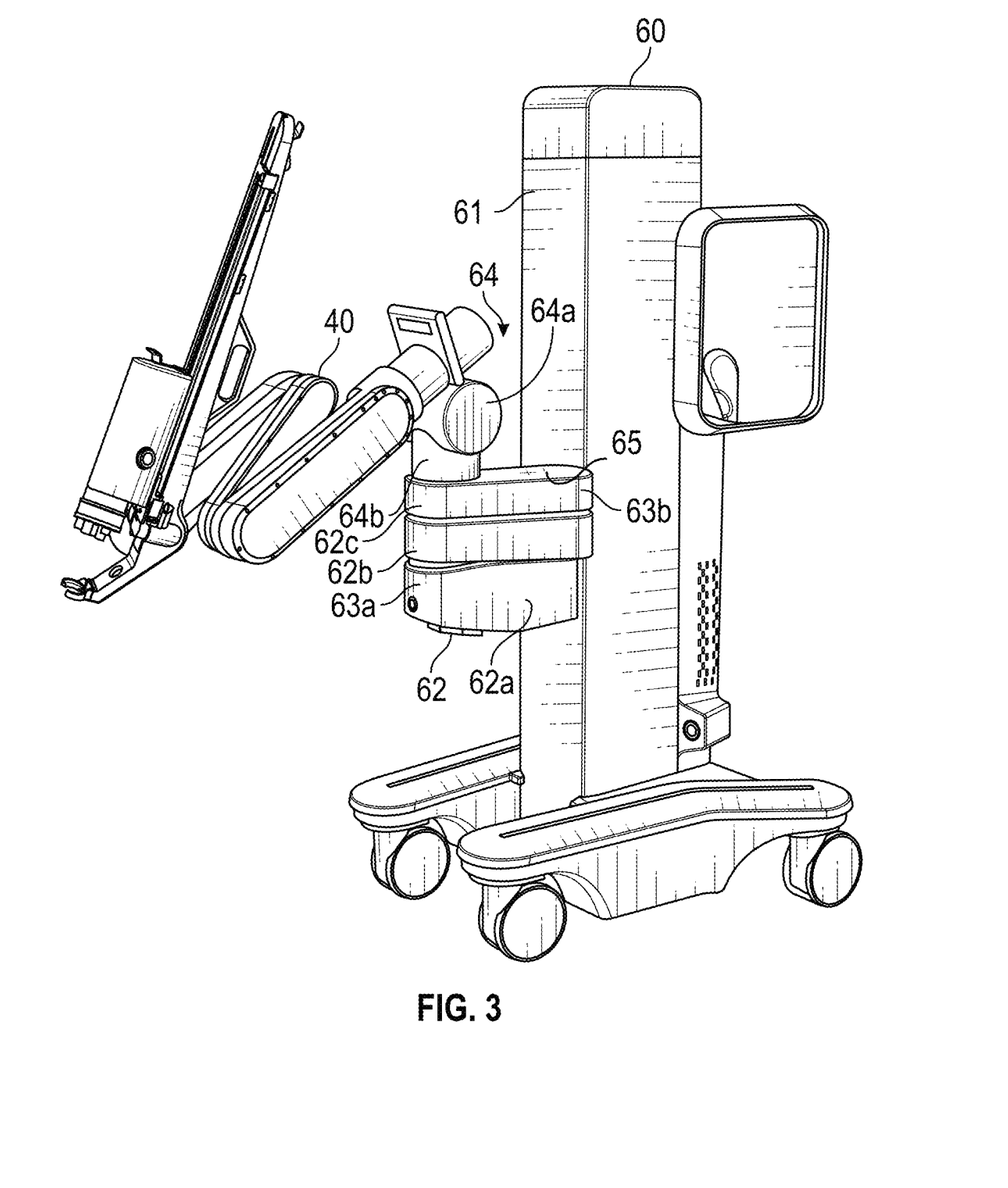
FIG. 3 is a perspective view of a setup arm with the surgical robotic arm of the surgical robotic system of FIG. 1 according to the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46a, which is configured to move the instrument drive unit 52 along the second longitudinal axis defined by the holder 46. The holder 46 also includes a joint 46b, which rotates the holder 46 relative to the link 42c.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

Figure 4:
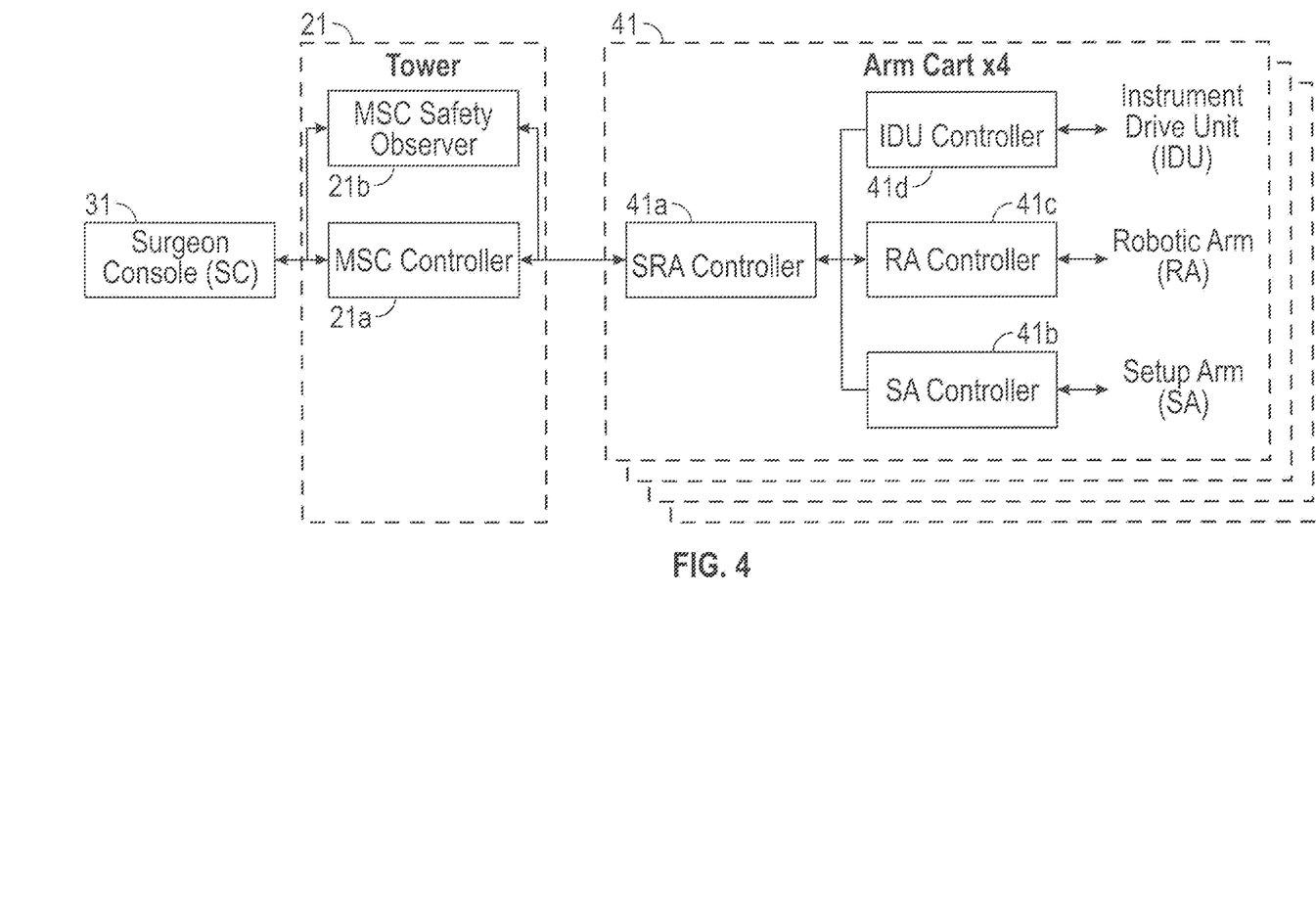
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the instrument drive unit 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the instrument drive unit 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the instrument drive unit 52. The IDU controller 41d calculates actual angles based on the motor positions and transmits these back to the main cart controller 41a.

The robotic arm controller 41c is also configured to estimate torque imparted on the joints 44a and 44b by the rigid link structure of the robotic arm 40, namely, the links 42a, 42b, 42c. Each of the joints 44a and 44b houses actuator 48a and 48b. High torque may be used to move the robotic arm 40 due to the heavy weight of the robotic arm 40. However, the torque may need to be adjusted to prevent damage or injury. This is particularly useful for limiting torque during collisions of the robotic arm 40 with external objects, such as other robotic arms, patient, staff, operating room equipment, etc.

In order to determine the effect of external torque on the robotic arm 40 the robotic arm controller 41c initially calculates frictional losses, gravitational forces, inertia, and then determines the effects of external torque. Once the external torque is calculated, the robotic arm controller 41c determines whether the environmental forces exceed a predetermined threshold which is indicative of collisions with external objects and takes precautionary action, such as terminating movement in the direction in which collision was detected, slowing down, and/or reversing movement (e.g., moving in an opposite direction) for a predetermined distance.

Figure 5:
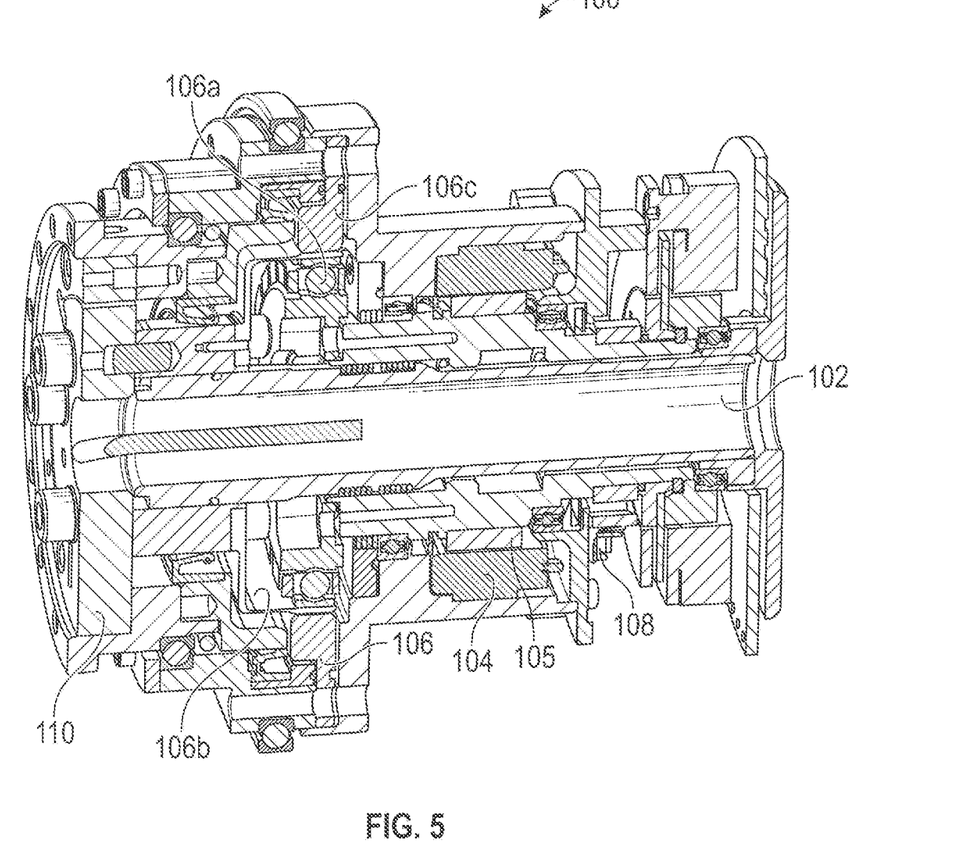
FIG. 5 is a cross-sectional view of an actuator of the surgical robotic arm of FIG. 2 according to the present disclosure.

The sensor measurements and calculations based thereon are described below with respect to FIG. 5, which shows an integrated joint module 100. The integrated joint module 100 may be used as the actuators 48a, 48b, 64a, 64b, and as the actuators within the joints 63a and 63b. The integrated joint module 100 includes a shaft 102, which acts as a support structure for the other components of the integrated joint module 100, namely, a motor 104 and a harmonic gearbox 106. The motor 104 may be any electric motor, which may be powered by AC or DC energy, such as a brushed motor, a brushless motor, a stepper motor, and the like. The motor 104 is coupled to the harmonic gearbox 106, which may be a harmonic drive gear configured to provide a large reduction ratio with approximately zero backlash, high torque capability, and high efficiency. The harmonic gearbox 106 may include concentric input and output shafts (not shown) and may include a wave generator 106a, disposed within a flexspline 106b having an outer geared surface, which is in turn, disposed within a circular spline 106c having an inner geared surface. As the motor 104 drives the wave generator 106a, the flexspline 106b, which may be formed from an elastic material, such as stainless steel, is also rotated. The flexspline 106b has fewer teeth than the circular spline 106c, therefore for every full rotation of the wave generator 106a, the flexspline 106b rotates less than a full rotation, which reduces the output speed. The harmonic gearbox 106 is in turn coupled to one of the belts 45a or 45b.

The integrated joint module 100 also includes a sensor suite for monitoring the performance of the integrated joint module 100 to provide for feedback and control thereof. In particular, the integrated joint module 100 includes an encoder 108 coupled to the motor 104. The encoder 108 may be any device that provides a sensor signal indicative of the number of rotations of the motor 104, such as a mechanical encoder or an optical encoder. The motor 104 may also include other sensors, such as a current sensor configured to measure the current draw of the motor 104, a motor torque sensor 105 for measuring motor torque, and the like. The number of rotations may be used to determine the speed and/or position control of individual joints 44a, 44b, 44c. Parameters which are measured and/or determined by the encoder 108 may include speed, distance, revolutions per minute, position, and the like. The integrated joint module 100 further includes a joint torque sensor 110 may be any force or strain sensor including one or more strain gauges configured to convert mechanical forces and/or strain into a sensor signal indicative of the torque imparted by the harmonic gearbox 106. The sensor signals from the encoder 108 and the joint torque sensor 110 are transmitted to the computer 41, which then controls the speed, angle, and/or position of each of the joints 44a, 44b, 44c of the robotic arm 40 based on the sensor signals. In embodiments, additional position sensors may also be used to determine movement and orientation of the robotic arm 40 and the setup arm 62. Suitable sensors include, but are not limited to, potentiometers coupled to movable components and configured to detect travel distances, Hall Effect sensors, accelerometers, and gyroscopes.

Figure 6:
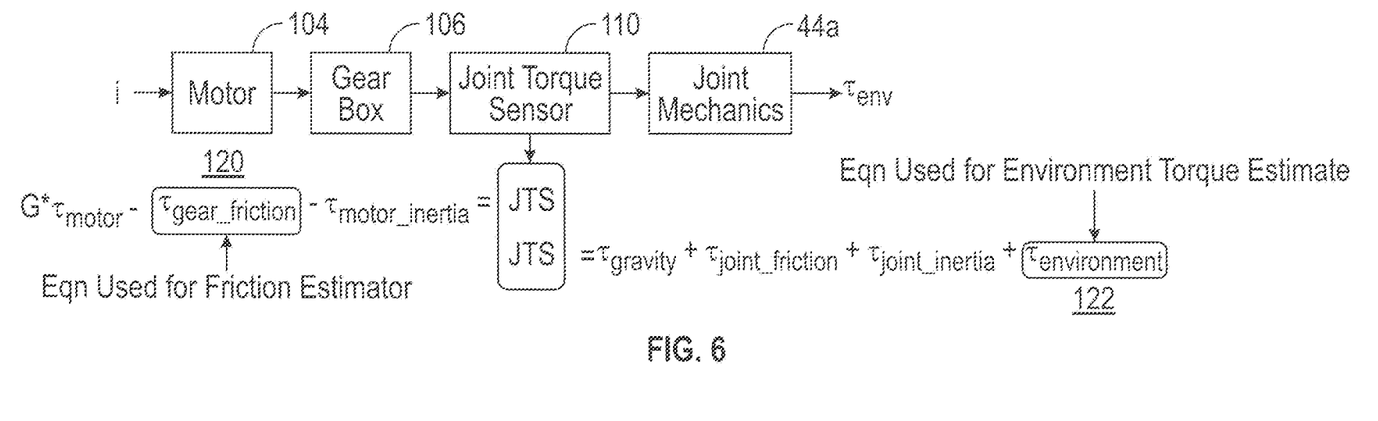
FIG. 6 is a schematic representation of torque measured by a torque sensor of the actuator of FIG. 5 according to the present disclosure.

With reference to FIG. 6, a dynamics model for the robotic arm 40 illustrates internal dynamics due to the motor torque imparted by the motor 104, which results in drive train inertia and friction due to change in rotational position of the motor 104. The motor torque also generates joint torque, e.g., at joints 44b and 44c, and changes to the link position of the links 42b, 42c, and the holder 46. The dynamics model also illustrates the effects of external torque on the robotic arm 40 due to external forces.

With continued reference to FIG. 6, a schematic diagram of the motor 104, the harmonic gearbox 106, and the joint torque sensor 110 is provided. As noted above, the joint torque sensor 110 measures the torque imparted on the joint, within which the joint torque sensor 110 is disposed, such as the joint 44a, 44b, 44c. The torque measured by the joint torque sensor 110 includes internal torque parameters, namely, the torque generated by the motor 104 accounting for gear friction of the harmonic gearbox 106 and motor inertia of the motor 104. In addition, the measured torque also includes external torque parameters, namely, effects of gravity on the links 42a, 42b, 42c (e.g., weight), joint friction and joint inertia of each of the joints 44a, 44b, 44c, as well as environmental torque, e.g., due to collision with objects. In order to determine the effect of external torque on the robotic arm 40 the robotic arm controller 41c initially calculates frictional losses, gravitational forces, inertia, and then determines the effects of external torque.

Each of the robotic arm controller 41c and the setup arm controller 41b includes a friction observer module, which calculates the frictional torque at the respective joints and actuators using the joint torque sensor 110, the angular speed from the encoder 108, and the motor torque from the motor torque sensor 105.

In embodiments, the friction observer module may use the measured torque from the joint torque sensor 110, commanded motor torque, and estimated motor inertia, which is calculated from the measured joint encoders, as shown in FIG. 6. In further embodiments, the friction observer module may use Coulomb and viscous friction model that uses the estimated velocity calculated from the joint encoders.

The friction observer module may calculate actual friction based on Coulomb friction, viscous friction, and dead zone of the joint torque sensor 110, which corresponds to the torque sensor offset. Coulomb friction is calculated based on a direction and magnitude of a friction force between two bodies in dry physical contact. Viscous friction is calculated based on a direction and magnitude of a friction force between two bodies in fluid physical contact. Dead zone corresponds to a certain portion of the inputs of the joint torque sensor 110 which produce a zero output.

The friction estimator module may be implemented in software, executable by the robotic arm controller 41c. The friction estimator module is based on the external torque applied on the joint 44b and measured by the joint torque sensor 110 measured at non-zero angular velocities (e.g., when the joint 44b is moving the joints 44a, 44b, 44c. Thus, the friction estimator module also receives angular speed from the encoder 108. In addition, the friction estimator module also utilizes motor torque from the motor torque sensor 105.

The friction estimator module may incorporate the following formulas (I) and (II):

$$u = J\ddot{\theta} + T_s + \hat{T}_{fm} \quad \text{(I)}$$

$$\hat{T}_{fm} = -LJ_m(\dot{\theta}_m - \dot{\theta}_m) \quad \text{(II)}$$

In formulas (I) and (II), "s" is the Laplace operator, "L" is the filter time constant, "$\hat{T}_{fm}$" is the estimated friction, "$T_{fm}$" is the actual friction. The Coulomb friction, viscous friction and torque sensor dead zone in the joint 44b is given by formula (III):

$$T_{fm} = f_c \cdot \text{sign}(\dot{\theta}) + f_v(\dot{\theta}) - f_d \cdot \text{sign}(\dot{\theta}) \quad \text{(III)}$$

In formula (III), "$f_c$" is the Coulomb friction coefficient, "$f_v$" is the viscous friction coefficient and "$f_d$" is the dead-zone friction (corresponds to torque sensor offset). The friction observer is defined by formulas (IV) and (V):

$$\hat{T}_{fm} = \frac{1}{(L^{-1}s + 1)} T_{fm} \quad \text{(IV)}$$

$$\hat{T}_{fm} = \left(\frac{1}{L^{-1}s + 1}\right)[f_c \cdot \text{sign}(\dot{\theta}) + f_v(\dot{\theta}) - f_d \cdot \text{sign}(\dot{\theta})] \quad \text{(V)}$$

The robotic arm controller 41c is also configured to calculate torque for compensating for the friction of the joint 44b as determined by the friction estimator module of the robotic arm controller 41c. In particular, the robotic arm controller 41c calculates the torque for the motor 104 that overcomes the friction encountered by the joint 44b. After determining the friction, the robotic arm controller 41c calculates a friction compensating torque or movement command for the motor 104 of the joint 44b that would be sufficient to overcome the friction.

The setup arm controller 41b is also configured to compensate for the friction acting on the actuators 64a, 64b and the joints 63a, 63b of the setup arm 62. The setup arm controller 41b calculates the torque for the motor 104 of the joints 63a, 63b, and the actuators 64a, 64b that would overcome the friction encountered by actuators 64a, 64b and the joints 63a, 63b. After determining the friction, the setup arm controller 41b calculates a friction compensating torque or movement command for the actuators 64a, 64b and the joints 63a, 63b of the setup arm 62 that would be sufficient to overcome the friction.

The method for friction compensation according to the present disclosure may be applied to the robotic arm 40 and/or the setup arm 62 and may be executed by either the robotic arm controller 41c or the setup arm controller 41b. With respect to the robotic arm 40, the movement command is received from the control tower 20, e.g., in response to a movement command from the surgical console 30. With respect to the setup arm 62, the movement command is received from the controls 65. The controller 21a of the control tower 20 processes these input positions to determine desired drive commands for each joint of the robotic arm 40 and/or the setup arm 62 and transmits the processed movement command to the computer 41. The computer 41, and in particular the robotic arm controller 41c, controls each joint 44a and 44b of the robotic arm 40 and calculates desired motor torques for the actuators 48a, 48b. Similarly, the setup arm controller 41b, controls each link 62a, 62b, 62c of the setup arm 62 and calculates motor torque for the actuators of the joints 63a and 63b and the actuators 64a, 64b. The motor torque includes sufficient torque to impart movement of the links 42a, 42b, 42c, 62a, 62b, 62c to match the movement command. In addition, the motor torque is also calculated to compensate for effects of friction on the joints 44a, 44b, 44c, 63a, 63b and the actuators 64a, 64b. Thus, the motor torque command includes two components, a first component for imparting movement corresponding to the movement command, and a second component corresponding to movement for overcoming friction of each of the motors 104 of the joints 44a, 44b, 44c, 63a, 63b and the actuators 64a, 64b. The second component is based on the calculated friction as described above. In particular, the friction estimator module of the computer 41 calculates the frictional torque at the joint 44b using the joint torque sensor 110, the angular speed from the encoder 108, and the motor torque from the motor torque sensor 105. In embodiments, commanded motor torque may be used in lieu of the measured motor torque.

Each of the robotic arm controller 41c and the setup arm controller 41b includes a gravity compensator module, which calculates the effects of gravity of the robotic arm 40 and setup arm 62, respectively. The robotic arm controller 41c is also configured to calculate torque for compensating for gravitational forces acting on the robotic arm 40, namely, the weight of the links 42a, 42b, 42c and other components of the robotic arm 40. The robotic arm controller 41c calculates the torque for the motor 104 that would statically balance the robotic arm 40 against the load of gravity by setting velocities and acceleration of the joints 44a, 44b, 44c to zero. This provides for a static modelling of the robotic arm 40 disregarding all movement of the robotic arm 40 other than the movement due to gravity. After determining the movement of the robotic arm 40 that is solely caused by gravity, the robotic arm controller 41c calculates a gravity compensating torque or movement command for the motor 104 of the actuators 48a and 48b that would be sufficient to cancel out the sagging of the robotic arm 40.

The setup arm controller 41b is also configured for compensating for gravitational forces acting on the setup arm 62, namely, the weight of the robotic arm 40 imparted on the rotatable base 64. The actuator 64a controls the pitch of the robotic arm 40, namely, the angle of the robotic arm 40 relative to the setup arm 62, and by extension the floor, as such since the actuator 64a has to work against gravity. The setup arm controller 41b calculates the torque for the actuator 64a that would statically balance the rotatable base 64 and the robotic arm 40 against the load of gravity by setting velocities and acceleration of the actuator 64a to zero. This provides for a static modelling of the setup arm 62 and the robotic arm 40 disregarding all movement of the robotic arm 40 other than the movement due to gravity. After determining the movement of the setup arm 62 and robotic arm 40 that is solely caused by gravity, the setup arm controller 41b calculates a gravity compensating torque or movement command for actuator 64a that would be sufficient to cancel out the sagging of the robotic arm 40 and compensate for the pitch.

The method for gravity compensation according to the present disclosure may be applied to the robotic arm 40 and/or the setup arm 62 and may be executed by either the robotic arm controller 41c or the setup arm controller 41b. With respect to the robotic arm 40 the movement command is received from the control tower 20, e.g., in response to a movement command from the surgical console 30. With respect to the setup arm 62 the movement command is received from the controls 65. The controller 21a of the control tower 20 processes these input positions to determine desired drive commands for each joint of the robotic arm 40 and/or the setup arm 62 and transmits the processed movement command to the computer 41. The computer 41, and in particular the robotic arm controller 41c, controls each joint 44a and 44b of the robotic arm 40 and calculates desired motor torques for the actuators 48a, 48b. Similarly, the setup arm controller 41b, controls each link 62a, 62b, 62c of the setup arm 62 and calculates motor torque for the actuators of the joints 63a and 63b. The motor torque includes sufficient torque to impart movement of the links 42a, 42b, 42c, 62a, 62b, 62c to match the movement command. In addition, the motor torque also is calculated to compensate for effects of gravity on the robotic arm 40, and in particular, for each of the links 42a, 42b, 42c, 62a, 62b, 62c and joints 44a, 44b, 44c, 63a, 63b. Thus, the motor torque command includes two components, a first component for imparting movement corresponding to the movement command and a second component corresponding to movement for compensating for gravity of each of the components of the robotic arm 40 and/or the setup arm 62.

The robotic arm controller 41c and the setup arm controller 41b calculate the torque for the actuators that would statically balance the robotic arm 40 and the setup arm 62 against the load of gravity by setting velocities and accelerations of the joints 44a, 44b, 44c and the actuator 64a to zero. The motor torque command includes a first component which includes motor torque for imparting movement which moves the robotic arm 40 and/or the setup arm 62 to a desired position and a second component which is configured to compensate for the effects of gravity. The second component is calculated by setting the values of the first component, namely, velocity and acceleration to zero. In addition, the second component is also based on the mass, rigidity, dimensions of the links 42a, 42b, 42c, 62a, 62b, 62c and angles therebetween.

The compensation process also includes calculating motor torque for actuators which are not directly impacted by the movement command, namely, those actuators whose actuation is not required for moving the joints 44a, 44b, 44c, 63a, 63b, since movement commands for moving the robotic arm 40 indirectly affect the joints 63a and 63b of the setup arm 62, which remain stationary and vice versa.

External torque compensation processes may be performed by the robotic arm controller 41c and may involve measuring output torque of a joint through the joint torque sensor 110, observing torque applied to the environment by the robotic arm 40, and adjusting movement of the robotic arm 40 based on changes in the external torque outside predetermined thresholds, which are indicative of external forces, such as collisions with objects.

With continued reference to FIG. 6, the joint torque sensor 110 measures the torque of a joint (e.g., joint 44a, 44b, 44c, etc.). The measured torque is representative of internal forces 120 and external forces 122. Internal forces 120 include motor torque generated by the motor 104 subtracting for mechanical losses such as gear friction of the harmonic gearbox 106 and motor inertia of the motor 104, which is calculated based on the angular speed of the motor 104. External forces 122 include gravity load, joint friction, and environmental torque. As used herein, the term "environmental torque" refers to any external forces acting on the robotic arm 40 besides gravity, friction, or inertia, such as those due to collision with objects in the operating room.

As noted above, each of the components of the internal forces 120 may be measured using joint torque sensor 110, the encoder 108, and the motor torque sensor 105 or otherwise calculated by the robotic arm controller 41c or the setup arm controller 41b using the friction estimator module and the gravity compensator module. In particular, the motor torque and motor inertia are measured by the motor torque sensor 105, the gear friction and the joint friction are calculated by the friction observer, and the gravity load is calculated by the gravity compensator module. Thus, after each of the above values are calculated and/or measured, each of the values is added to determine an estimated joint torque value. The estimated joint torque value is then compared by the robotic arm controller 41c or the setup arm controller 41b with measured torque value. As noted above, the measured torque value, which is measured by the joint torque sensor 110, measures all of the components of the estimated joint torque value as well as any forces imparted by the environmental torque. The robotic arm controller 41c or the setup arm controller 41b then calculates the environmental torque by subtracting the calculated joint torque from the measured joint torque.

Environmental torque may be calculated using an inverse dynamics calculation representative of the robotic arm 40 and the setup arm 62. The inverse dynamics calculation is based on instantaneous positions, velocities and the accelerations of the robotic joints (e.g., joints 44a, 44b, 44c, etc.). The instantaneous motor torques and forces driving the joints are computed by the robotic arm controller 41c or the setup arm controller 41b. The robotic arm controller 41c or the setup arm controller 41b also store various link parameters, including masses and inertias for each of the each of the links 42a, 42b, 42c, 62a, 62b, 62c, respectively, as well kinematic relations between the links. Once the inverse dynamics function is computed, the gravity compensation part is separated out by substituting zeros for the velocities and the accelerations.

The inverse dynamics problem for the robotic arm 40 and the setup arm 62 may be solved using Lagrangian mechanics. In deriving the kinematic relations between link frames, active/independent joint variables are used. In other words, the constrained/dependent link positions/orientations are expressed in terms of the independent joint variables using the constraint relations. This allows incorporation of the constraints early on in the frame definitions and eliminates the need to include constraint equations in Lagrange formulation.

For each link 42a, 42b, 42c mass, center of mass and inertia tensors may be defined with respect to a local reference frame of the link. Each link 42a, 42b, 42c is defined as a rigid body having the following attributes: a local coordinate frame for the link, center of mass of the link described in the local coordinate frame, and inertia of the link around its center of mass, defined in the local reference frame.

The kinematic relations between the local reference frames of the links 42a, 42b, 42c are constructed according to the frame definitions noted above. An inertial reference frame is chosen, which coincides with the rotatable base 64 when the pitch angle is 0. The total kinetic energy (K) of the robotic arm 40 resulting from kinetic energies of the links 42a, 42b, 42c due to their translational and rotational motion in the reference frame is derived. Likewise, the total potential energy (P) of the system is also calculated with respect to a common point in the world frame. Once these terms are computed, the Lagrangian is defined in formula (VI) below:

$$T = K - P \quad \text{(VI)}$$

Having the Lagrangian for the robotic arm 40, the generalized equations of motion (Lagrange equations) are defined by formula (VII) below:

$$Q_j = \frac{d}{dt}\left(\frac{\partial T}{\partial \dot{q}_j}\right) - \left(\frac{\partial T}{\partial q_j}\right) \quad \text{(VII)}$$

Once the inverse dynamics function is calculated, the results of the function can be compared against the measured torques force at the links 42a, 42b, 42c and joints 44a, 44b, 44c in order to estimate the external torque/force applied by the robotic arm 40 to the environment.

Figure 7:
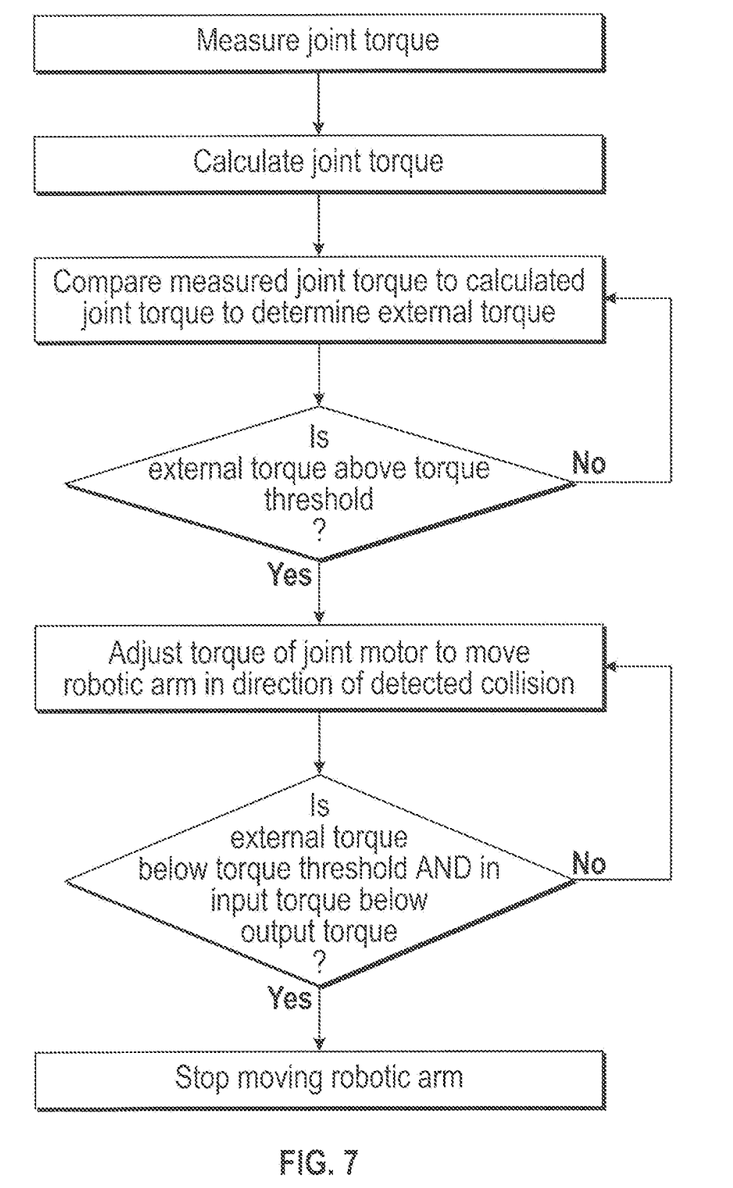
FIG. 7 is a method for detecting collisions of the surgical robotic arm and controlling the surgical robotic arm in response thereto according to the present disclosure.

With reference to FIG. 7, the present disclosure also provides a method for responding to a collision after detection thereof. Initially, a collision is detected based on calculating external torque force as described above. The calculated external torque is then compared to an external torque threshold. In embodiments, the threshold may be from about 10 Newton meters (Nm) to about 20 Nm, in further embodiments, the threshold may be about 15 Nm. If the calculated external torque exceeds the threshold, the robotic arm controller 41c then adjusts or shuts off movement of the surgical robotic arm 40.

The method may be embodied in software and may be executed by any of the computers 21, 31, 41. Similar to the friction and gravity compensation methods disclosed above, with respect to the robotic arm 40 the movement command is received from the control tower 20, e.g., in response to a movement command from the surgical console 30. With respect to the setup arm 62 the movement command is received from the controls 65. The controller 21a of the control tower 20 processes these input positions to determine desired drive commands for each joint of the robotic arm 40 and/or the setup arm 62 and transmits the processed movement command to the computer 41. The computer 41, and in particular the robotic arm controller 41c, controls each joint 44a and 44b of the robotic arm 40 and calculates input motor torque for the actuators 48a, 48b. Similarly, the setup arm controller 41b, controls each link 62a, 62b, 62c of the setup arm 62 and calculates input motor torque for the actuators of the joints 63a and 63b. The input motor torque includes sufficient torque to impart movement of the links 42a, 42b, 42c, 62a, 62b, 62c to match the movement command.

As the surgical robotic arm 40 is moved in response to the movement command, the method calculates external torque that is encountered by the surgical robotic arm 40 during its movement. The method also includes calculating the estimated joint torque as described above. In particular, each of the components of the internal forces 120 may be measured using joint torque sensor 110, the encoder 108, and the motor torque from the motor torque sensor 105 or commanded motor torque or otherwise calculated by the robotic arm controller 41c or the setup arm controller 41b using the friction estimator module and the gravity compensator module. The motor inertia is calculated using the encoder values and rotor inertia, the gear friction and the joint friction are calculated by the friction observer, and the gravity load is calculated by the gravity compensator module. The friction observer module calculates the motor and gearbox friction, while the joint friction is a separate model. Thus, after each of the above values are calculated and/or measured, each of the values is added to determine an estimated joint torque value. The estimated joint torque value is then compared by the robotic arm controller 41c with measured torque value. The robotic arm controller 41c then calculates the environmental torque by subtracting the calculated joint torque from the measured joint torque.

The environmental torque is then compared to a threshold to determine whether there is a collision. The threshold is used to filter out false readings such that only environmental torque due to collision triggers a positive response. After the collision is detected, the robotic arm controller 41c adjusts the commanded motor torque in a direction of the detected collision. In embodiments, position control, namely, execution of the movement command may be suspended or terminated in response to detection of the collision. In addition, the robotic arm controller 41c also prevents oversaturing the torque of the motor 104. After it is determined that the external torque is below the threshold indicative of collision, the robotic arm controller 41c stops the surgical robotic arm 40 by setting input motor torque to zero while continuing to output torque to compensate for gravity and friction in a collision state. This prevents the surgical robotic arm 40 from lurching in the direction of movement prior to the collision once the obstacle has been removed.

Figure 8:
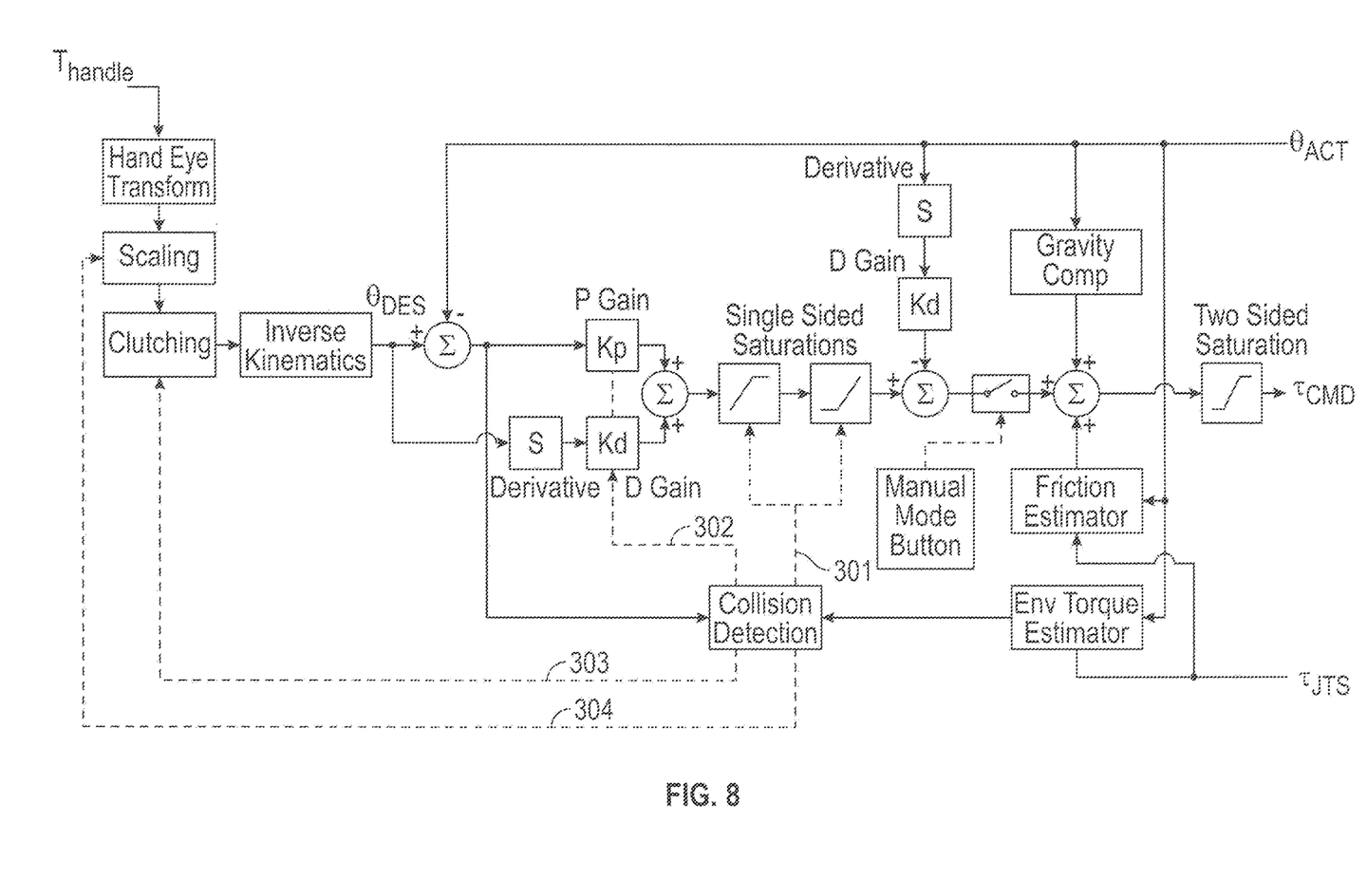
FIG. 8 is a flow chart for controlling the surgical robotic arm according to one embodiment of the present disclosure.

FIG. 8 shows a flow chart diagram of a kinematic controller for controlling the robotic arm 40. Initially, a pose of the handle controller controlling the robotic arm 40, e.g., the handle controller 38a, is transformed into a desired pose of the robotic arm 40 through a hand eye transform function executed by the main cart controller 41a. The hand eye function, as well as other functions described herein, is/are embodied in software executable by the main cart controller 41a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the main cart controller 41a. In embodiments, the coordinate position is scaled down and the orientation is scaled up by the scaling function. In addition, the main cart controller 41a also executes a clutching function, which disengages the handle controller 38a from the robotic arm 40. In particular, the main cart controller 41a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the main cart controller 41a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller. The joint axis controller includes a proportional-derivative (PD) controller, the friction estimator module, the gravity compensator module, and a two-sided saturation block, which is configured to limit the commanded torque of the motor 104. The joint axis controller also includes an environment torque estimator module, which determines the force and/or torque that the robotic arm 40 and the surgical instrument 50 is applying to the environment, such as the patient, other robotic arms 40, operating table, bedside operator, and other objects or people.

In one embodiment, the environment torque estimator module is configured to calculate an estimated environmental torque based on a sensor signal from $\tau$JTS the joint torque sensor 110 as described above. In another embodiment, the environment torque estimator may be implemented based on position error alone or in combination with the sensor signal $\tau$JTS from the joint torque sensor 110. In another embodiment, the environment torque estimator may use actual position and velocity of the robotic arm 40 as well as a computed model of the gravity and friction from the friction estimator module and the gravity compensator module, respectively.

The estimated environmental torque is supplied to a collision detection module executed by the robotic arm controller 41c. The collision detection module determines whether the robotic arm 40 collided with an external object or person based on the estimated environmental torque and enters a collision state if the estimated environmental torque value exceeds a first torque threshold, which in embodiments may be +/−15 Nm. The collision state is active until the estimated environment torque drops below a second torque threshold and a position error of the robotic arm 40 is minimal, which in embodiments is within +/−1 degree of the desired position angle for each of the joints or the sum of error for each angle is +/−5 degrees. The second threshold is smaller than the first torque threshold and in embodiments may be +/−5 Nm. The verification of the decrease in environmental torque and the error of the position angle ensures that the robotic arm 40 does not accelerate quickly to a desired position further from the current position based on the position of the handle controller 38a.

In further embodiments, entry into the collision state may occur if the environment torque is greater than the first threshold, the desired (i.e. commanded) speed is above a speed threshold, which may be about 1 degree per second, and the direction of the environment torque is opposite the direction of the desired velocity. The last condition accounts for a situation where the arm is moving into the collision and not getting pushed by an operator at the bedside. Using these three parameter thresholds keeps the robotic arm 40 stiff while the robotic arm 40 is stationary and holding its position and minimizes collision forces when the robotic arm 40 is actively being driven during teleoperation.

During the collision state, the joint axis controller continues to apply the full amount of torque to compensate for gravity and friction of the joints as described above. In response to friction and gravity compensation, the robotic arm 40 continues to maintain its position similar to when the robotic arm 40 is put in manual mode. A portion of the PD controller which generates damping, e.g., negative feedback of the actual velocity, is not limited by the single-sided saturation block.

While the collision state is active, the robotic arm controller 41c communicates to the computers 21, 31, 41 of the surgical robotic system 10 to limit the applied force. In embodiments, this may be done by limiting the commanded torque component generated by the PD controller as shown by a command line 301. The limiting command is generated by the collision detection module and may be split into two single-sided saturations such that the limit can be applied in the direction of the detected collision. This allows motion away from the collision to not be limited, such that the robotic arm 40 retains full performance to move away from the collision. When in a collision state, the single-sided saturations can be set to zero, meaning no torque is applied due to position errors, or to a small torque level allowing for a gentle pressure of the arm against the environment.

Additional control schemes for responding to collisions also include commands issued by the collision detection module represented as the command lines 302, 303, 304. With respect to the command line 302, the collision detection module may alter (e.g., lower) the P and/or D gain of the joint axis controller. This would produce less torque due to position errors when in a collision state. Regarding command line 303, the collision detection module may alter the desired motion of the robotic arm 40 by "clutching out" the handle controller 38a in the direction of the collision, e.g., using clutching function to disengage the handle controller 38a from the robotic arm 40. This would cause the robot arm 40 to stop moving in the direction of the collision, but allow full force to move away from the collision. In command line 304, the collision detection module may alter the scaling factor (e.g., increase) to slow down the motion of the robotic arm 40 in the direction of the collision. This approach could also use a dynamic scaling factor that increases as the environment torque increases. This would make the robotic arm 40 slow down as the robotic arm 40 applies higher force and torque to the environment.

In embodiments, the set position point (i.e., desired or commanded position) of a joint may be changed if the robotic arm 40 and/or a specific joint are pushed too far away from the set position point, which is reflected as a tracking position error in order to minimize the "spring back" of the robotic arm due to the movement comments from the robotic arm controller 41c. This configuration deals with a situation in which an operator leans on and as result deflects the robotic arm 40, it would be undesirable for the robotic arm 40 to suddenly move back to the desired position after the operator removes the force displacing the robotic arm. The updated set point described above could be equal to the current position or a small distance away from the current position such that the tracking error has the same commanded torque but minimizes the spring back distance. In further embodiments, if the tracking error is too large, the handle controller 38a is "clutched out" in the direction of the error, e.g., using clutching function to disengage the handle controller 38a from the robotic arm 40.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

The invention claimed is:

1. A surgical robotic arm comprising:
a first link;
a second link coupled to the first link at a first joint such that at least one of the first link or the second link is movable relative to each other;
a first actuator configured to move at least one of the first link or the second link;
a joint torque sensor disposed within the first joint and configured to measure torque imparted on at least one of the first link or the second link to obtain a measured torque value; and
a controller configured to:
calculate an input motor torque command in response to a movement command, the input motor torque command configured to activate the first actuator to move at least one of the first link or the second link according to the movement command;
determine an estimated joint torque value;
determine an environmental torque value based on a difference between the estimated joint torque value and the measured torque value;
detect a collision based on the environmental torque value being above a first threshold; and
enter a collision state in response to the environmental torque value being above the first threshold, wherein while in the collision state, the controller is further configured to:
adjust the input motor torque command to prevent oversaturating output torque of the first actuator; and
determine the collision state is terminated based on the environmental torque value being below a second threshold and a position error being below a position error threshold.

2. The surgical robotic arm according to claim 1, wherein the second threshold is smaller than the first threshold.

3. A surgical robotic arm comprising:
at least one movable link coupled to a joint;
an actuator configured to move the at least one movable link relative to the joint;
a joint torque sensor configured to measure torque imparted on the at least one movable link to obtain a measured torque value; and
a controller configured to:
calculate an input motor torque command in response to a movement command, the input motor torque command configured to activate the actuator to move the at least one movable link according to the movement command;
determine an estimated joint torque value;
determine an environmental torque value based on a difference between the estimated joint torque value and the measured torque value;
detect a collision based on the environmental torque value being above a first threshold; and
enter a collision state in response to the environmental torque value being above the first threshold, wherein while in the collision state, the controller is further configured to:
adjust the input motor torque command to prevent oversaturating output torque of the actuator; and
determine the collision state is terminated based on the environmental torque value being below a second threshold and a position error being below a position error threshold.

4. The surgical robotic arm according to claim 3, wherein the second threshold is smaller than the first threshold.

5. A method for detecting collision of a surgical robotic arm, the method comprising:
transmitting a movement command to the surgical robotic arm including an actuator configured to move at least one movable link relative to a joint;
measuring torque imparted on the at least one movable link to obtain a measured torque value;
calculating an input motor torque command in response to a movement command, the input motor torque command configured to activate the actuator to move the at least one movable link according to the movement command;
determining an estimated joint torque value;
determining an environmental torque value based on a difference between the estimated joint torque value and the measured torque value;
detecting a collision based on the environmental torque value being above a first threshold;
entering the surgical robotic arm into a collision state in response to the environmental torque value being above the first threshold, wherein while in the collision state, adjusting the input motor torque command to prevent oversaturating output torque of the actuator; and
while in the collision state, determining the collision state is terminated based on the environmental torque value being below a second threshold and a position error being below a position error threshold.

6. The method according to claim 5, wherein the second threshold is smaller than the first threshold.

* * * * *